United States Patent [19]
Augustine

[11] Patent Number: 5,824,025
[45] Date of Patent: Oct. 20, 1998

[54] SYSTEM FOR CONVECTIVE WARMING OF A PATIENT DURING CARDIAC SURGERY

[75] Inventor: Scott D. Augustine, Bloomington, Minn.

[73] Assignee: Augustine Medical, Inc., Eden Prairie, Minn.

[21] Appl. No.: 915,277

[22] Filed: Aug. 20, 1997

[51] Int. Cl.⁶ .................................................. A61F 7/00
[52] U.S. Cl. .................................................. 607/107
[58] Field of Search .................... 607/96, 104, 107; 165/46; 5/482, 423; 128/849, 850, 855

[56] References Cited

U.S. PATENT DOCUMENTS

| | | | |
|---|---|---|---|
| 222,690 | 12/1879 | Goldschmidt . | |
| 1,399,095 | 12/1921 | Webb, Sr. . | |
| 1,777,982 | 10/1930 | Popp . | |
| 2,093,834 | 9/1937 | Gaugler | 128/145 |
| 2,110,022 | 3/1938 | Kliesrath | 5/334 |
| 2,122,964 | 7/1938 | Sweetland | 34/26 |
| 2,512,559 | 6/1950 | Williams | 5/347 |
| 2,601,189 | 6/1952 | Wales, Jr. | 4/160 |
| 2,706,988 | 4/1955 | Weber | 128/402 |
| 3,243,827 | 4/1966 | Kintner | 5/334 |
| 3,418,726 | 12/1968 | Sparks | 34/99 |
| 3,610,251 | 10/1971 | Sanderson | 128/379 |

(List continued on next page.)

FOREIGN PATENT DOCUMENTS

| | | |
|---|---|---|
| 0 311 336 | 8/1988 | European Pat. Off. . |
| 33 08 553 | 3/1983 | Germany . |
| 0 113 420 | 11/1983 | Germany . |
| 716746 | 10/1954 | United Kingdom . |
| 1 334 935 | 3/1971 | United Kingdom . |
| 1 461 383 | 4/1973 | United Kingdom . |
| 1 532 219 | 6/1975 | United Kingdom . |
| 1 566 207 | 5/1977 | United Kingdom . |
| WO 85/03216 | 8/1985 | WIPO . |

OTHER PUBLICATIONS

Webster's Ninth New Collegiate Dictionary definition of "laminate".
Webster's Third New International Dictionary, p. 250, definition of "bonding".
McGraw–Hill Encyclopedia of Science & Technology, 7th Ed., p. 713, definition of "bondong".
"NORMOTHERMIA IN THE OR" Augustine Medical, Inc., Oct. 1989.

Primary Examiner—George Manuel
Attorney, Agent, or Firm—Gray Cary Ware Freidenrich

[57] ABSTRACT

A warming system is provided for convectively warming a patient during a progressive medical procedure, such as cardiac surgery. The system includes one or more inflatable thermal blankets that are adjustably configurable to cover one or both of a patient's legs. Each thermal blanket includes an inflatable covering formed from an upper sheet and a base sheet attached at a plurality of locations. The base sheet includes a plurality of apertures that direct an inflating medium from the inflatable covering toward the patient. A portion of each thermal blanket is initially furled using a retaining device that prevents an inflating medium from inflating the furled portion. The non-furled portion of each thermal blanket is allowed to inflate and cover a patient. Prior to inflation, the furled portion of each thermal blanket defines a thermal blanket edge with demarcates an access area for a surgical procedure. When the retaining strip is removed, the furled portion is unfurled by action of the inflating medium and self erects into a continuation of the previously inflated non-furled portion of the thermal blanket to cover the surgical access site. A surgical drape may be placed over the tops of the thermal blankets in order to properly position each blanket on the patient, to maintain the temperature controlled medium proximate to the patient, and to perform the usual barrier functions of a drape. In the operation, a heater/blower that includes a compressor and a heater supplies heated air, under pressure, to an inlet opening in the one or more inflatable thermal blankets. The heated, pressurized air is distributed throughout each inflatable blanket, and flows to the patient through the apertures in the blanket's base sheet.

16 Claims, 14 Drawing Sheets

U.S. PATENT DOCUMENTS

| | | | |
|---|---|---|---|
| 3,610,323 | 10/1971 | Troyer | 165/46 |
| 3,691,646 | 9/1972 | Ruffolo | 34/90 |
| 3,714,947 | 2/1973 | Hardy | 128/400 |
| 3,757,366 | 9/1973 | Sacher | 5/347 |
| 4,572,188 | 2/1986 | Augustine et al. | 128/380 |
| 4,660,388 | 4/1987 | Greene, Jr. | 62/261 |
| 4,777,802 | 10/1988 | Feher | 62/3 |
| 4,807,644 | 2/1989 | Sandhaus | 128/849 |
| 4,867,230 | 9/1989 | Voss | 165/46 |
| 5,125,238 | 6/1992 | Ragan et al. | 62/259.3 |
| 5,184,612 | 2/1993 | Augustine | 128/400 |
| 5,300,100 | 4/1994 | Hickle et al. | 607/107 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/421 |
| 5,350,417 | 9/1994 | Augustine | 607/104 |
| 5,360,439 | 11/1994 | Dickerhoff et al. | 607/104 |
| 5,384,924 | 1/1995 | Dickerhoff et al. | 5/421 |
| 5,405,370 | 4/1995 | Irani | 607/107 |
| 5,405,371 | 4/1995 | Augustine et al. | 607/107 |
| 5,443,488 | 8/1995 | Namenye et al. | 607/104 |
| 5,514,169 | 5/1996 | Dickerhoff et al. | 607/107 |
| 5,545,194 | 8/1996 | Augustine | 607/104 |
| 5,596,778 | 1/1997 | Suzuki et al. | 5/502 |
| 5,620,482 | 4/1997 | Augustine et al. | 607/107 |
| 5,658,325 | 8/1997 | Augustine | 607/107 |
| 5,697,963 | 12/1997 | Augustine | 607/108 |
| 5,728,145 | 3/1998 | Phlipot et al. | 607/104 |
| 5,733,318 | 3/1998 | Augustine | 607/104 |

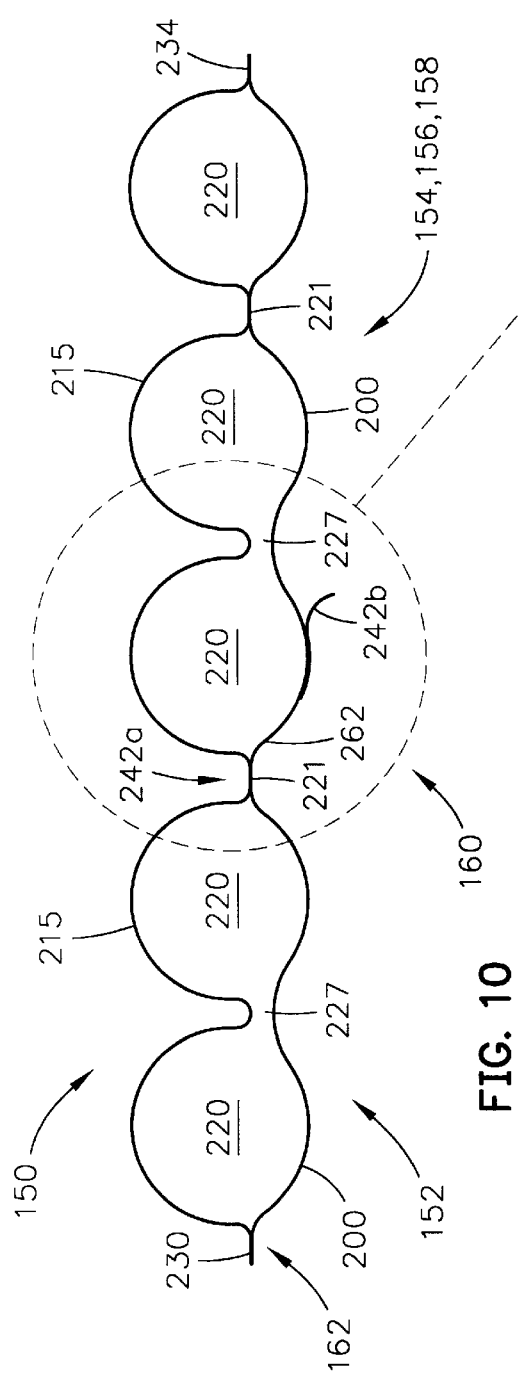
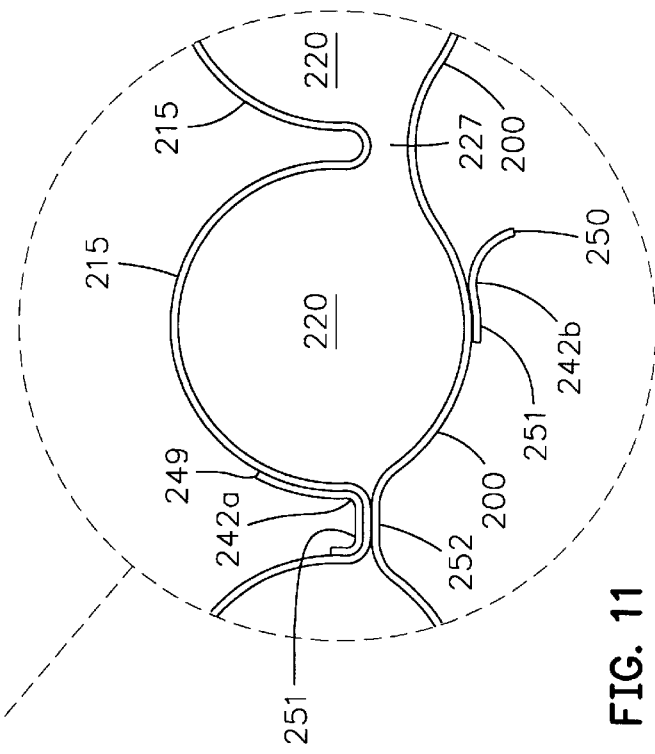
FIG. 10
FIG. 11

SYSTEM FOR CONVECTIVE WARMING OF A PATIENT DURING CARDIAC SURGERY

BACKGROUND OF THE INVENTION

1. Field of the Invention

This invention relates generally to the convective application of heat in a medical setting by delivery of a bath of a thermally-controlled gaseous medium, such as warmed air, to a patient. More particularly, the invention pertains to the use of inflatable blankets and surgical drapes to control body temperature during a medical procedure, while providing access to the patient for medical purposes such as cardiac surgery.

2. Description of the Related Art

The construction and operation of inflatable thermal blankets for convective warming of patients is disclosed in commonly-assigned U.S. Pat. No. 4,572,188 entitled "AIRFLOW COVER FOR CONTROLLING BODY TEMPERATURE," and U.S. Pat. No. 5,405,371 entitled "THERMAL BLANKET". These two patents describe thermal blankets that include a plurality of communicating inflatable chambers and apertures that open through lower blanket surfaces into the chambers. When inflated with warmed air, the pressure of the air in the chambers causes the thermal blankets to inflate. The apertures that open through the bottoms of the thermal blankets exhaust the warmed air onto the patient. Therefore, these inflatable thermal blankets create an ambient environment about the patient, the thermal characteristics of which are determined by the temperature and pressure of the gaseous inflating medium. One use for an inflatable thermal blanket is the maintenance of patient normothermia during a medical procedure, such as surgery.

The typical inflatable thermal blanket covers all, or much of, the patient's body, and it is not always possible to simultaneously access the patient, for medical purposes, while the blanket lays over the patient and provides temperature regulation.

The difficulty in providing patient access through an inflatable thermal blanket utilizing super atmospheric temperature controlled air is that such access interferes with the thermal regulation desired to be achieved by the blanket. This is especially significant during cardiac surgery when access must often be initially provided to the legs so that segments of a patient's leg veins can be removed and transplanted to the heart. In this respect, cardiac surgery is a progressive procedure, in that it progresses from an initial site (the legs), through intermediate sites (possibly), to a terminal site (the chest). Once the leg vein segments are removed, access to the legs is no longer required yet there is no ability to direct temperature controlled air to the leg area, unless a separate thermal blanket is placed over the legs. Placing a new thermal blanket over the legs, however, raises the issue of how to effectively attach and seal the blanket to the patient, without disrupting the procedure, so as to contain the temperature controlled air and achieve effective thermal regulation of the patient.

Accordingly, a need exists for a warming system that is capable of delivering a temperature-controlled airflow to a patient during a progressive medical procedure, such as cardiac surgery, so as to maintain the patient's body temperature at a desired level while simultaneously allowing initial access to one or more areas of the patient's body, following which the one or more areas can be covered for additional temperature control. What is required is a system that, while warming first portions of a patient's body, allows initial unimpaired medical access to, and subsequent temperature control of, other portions of the patient's body, without jeopardizing the patient's health or comfort during a medical procedure.

SUMMARY OF THE INVENTION

In order to overcome the limitations of the prior art, a system is provided for convectively warming a patient during a progressive medical procedure, such as cardiac surgery. The system of this invention comprises one or more inflatable thermal blankets that are adjustably configurable to cover a patient's legs. Each inflatable thermal blanket includes an inflatable covering formed by attaching an upper sheet to a base sheet at a plurality of locations. The base sheet includes a plurality of apertures that exhaust a warmed inflating medium from the inflatable structure toward the patient. A portion of each inflatable thermal blanket is initially furled using a retaining strip that prevents an inflating medium from inflating the furled portion. The non-furled portion of each inflatable thermal blanket is allowed to inflate and cover a patient. Prior to inflation, the furled portion of each thermal blanket defines a thermal blanket edge with demarcates an access area for a surgical procedure. When the retaining strip is removed, the furled portion is unfurled by action of the inflating medium and self erects into a continuation of the previously inflated non-furled portion of the thermal blanket to cover the surgical access site. A surgical drape may be placed over the top of the one or more inflatable thermal blankets to properly position the blanket(s) on the patient, to maintain the warmed inflatable medium proximate to the patient, and to perform the usual barrier functions of a drape.

In the operation of a preferred embodiment, a heater/blower that includes a compressor and a heater supplies heated air, under pressure, to an inflation inlet opening in each of the one or more thermal blankets. The heated, pressurized air is distributed throughout each inflatable blanket and flows to the patient through the base sheet apertures of the thermal blanket.

The foregoing, together with other objects, features and advantages of this invention, will become more apparent when referring to the following specification, claims and the accompanying drawings.

BRIEF DESCRIPTION OF THE PREFERRED EMBODIMENT

For a more complete understanding of this invention, reference is now made to the following detailed description of the embodiments as illustrated in the accompanying drawing, wherein:

FIG. 10 is a cross-sectional view taken along line B—B in FIG. 9;

FIG. 11 is an enlargement of a portion of the cross-sectional view of FIG. 10;

DETAILED DESCRIPTION OF THE PREFERRED EMBODIMENT

This invention is described in a preferred embodiment in the following description with reference to the Figures, in which like numbers represent the same or similar elements. While this invention is described in terms of a best mode for practice, it will be appreciated by those skilled in the art that variations may be accomplished in view of these teachings without deviating from the spirit or scope of the invention.

Figure 1:
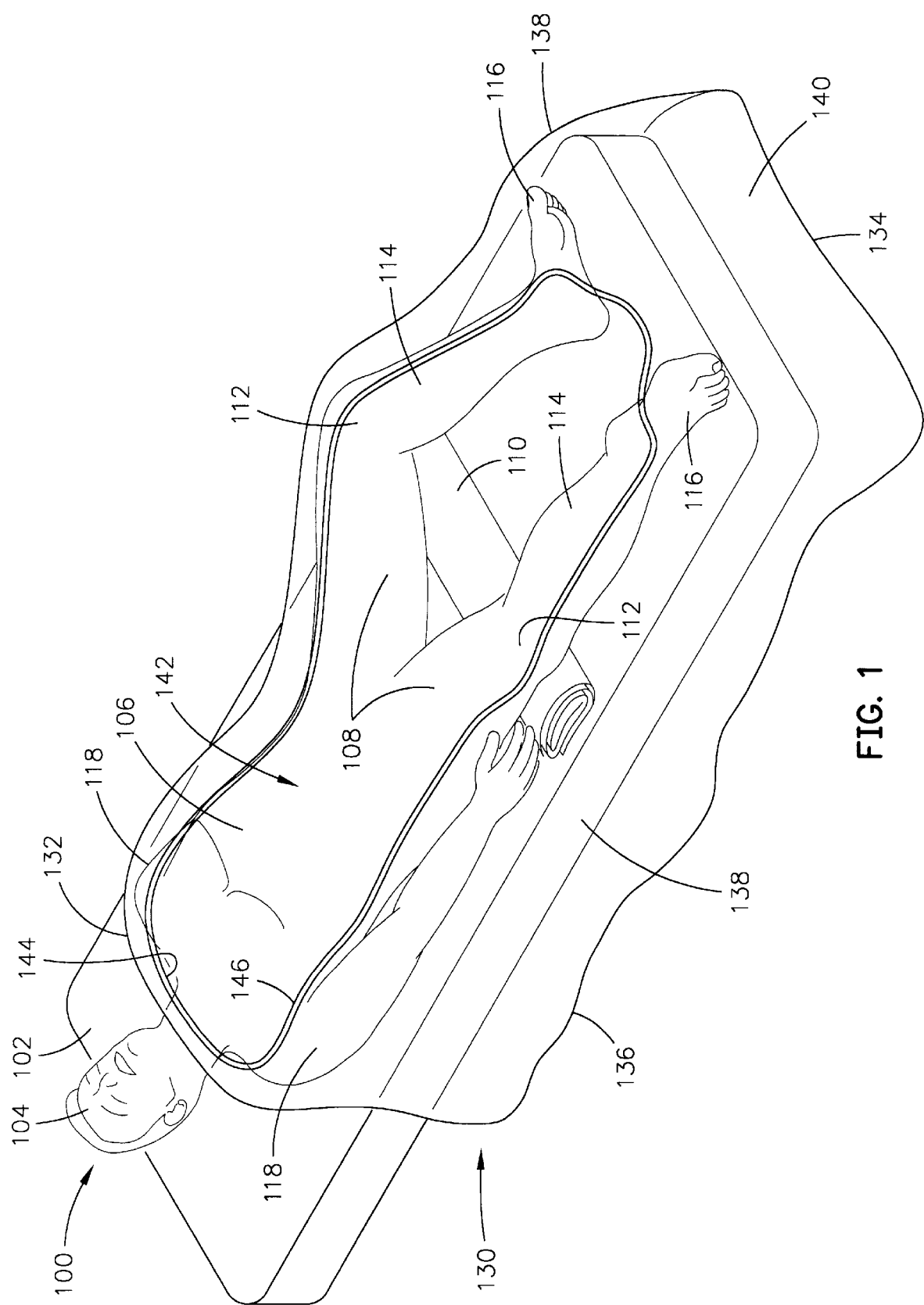
FIG. 1 is a perspective view of a supine patient covered by a surgical drape.

FIG. 1 illustrates a patient 100 in a supine position on a surgical table 102. The surgical table 102 may be in an operating room any other suitable location for cardiac surgery. The patient 100 is illustrated with his head 104 positioned generally supine, his torso 106 positioned generally supine, and his thighs 108 angled generally upwardly and apart by a support 110 which may be a rolled blanket or any other suitable article. The patient's knees 112 are slightly bent and his lower legs 114 extend downwardly while his feet 116 rest upon the table 102. The patient's arms 118 are illustrated drawn in to his sides.

A surgical drape 130 is shown as it might be placed over the patient 100 to cover the patient during cardiac surgery. The surgical drape includes a head end 132, a foot end 134 and lateral edges 136 (only one is shown). The surgical drape may be constructed as a single flat sheet with or without seams, or as multiple sheets so as to provide a pair of sides 138 and a end wall 140 located near the foot end 134. To provide access from the torso 106 to the lower legs 114 of the patient 100 for cardiac surgery, a large opening 142 is formed in the surgical drape 130. The opening 142 extends from a location adjacent the head end 132 to a location adjacent the top of the end wall 140. The opening 142 is defined by a continuous edge seam 144 that extends around the periphery of the opening in the shape of a rectangle. An attachment device, such as an adhesive seal 146, may be provided at selected portions of the edge seam 144 in order to secure the surgical drape 130 for use and to separate the exposed surgical site from the portions of the patient's body that are covered by the surgical drape.

Figure 2:
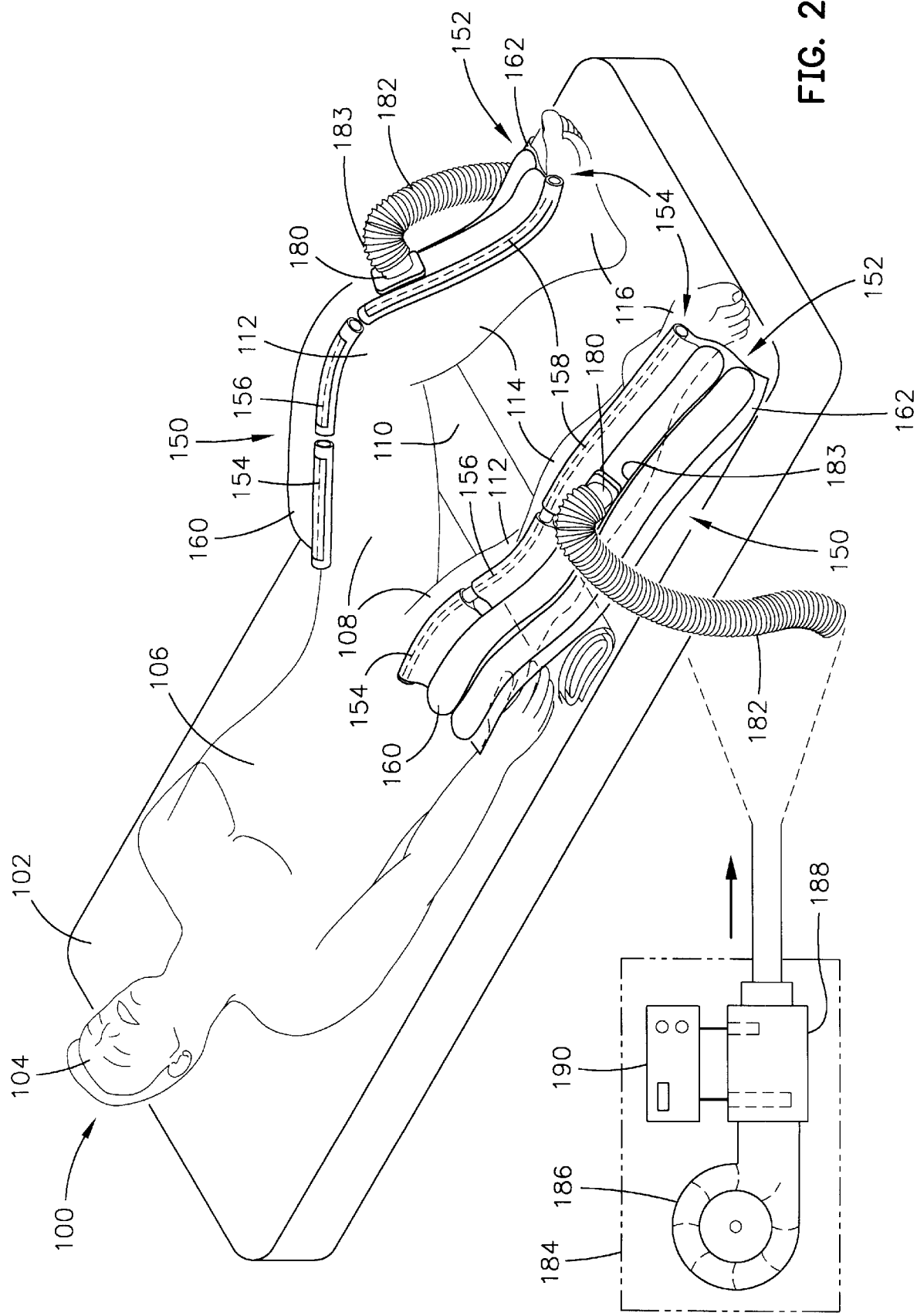
FIG. 2 is a perspective view of a supine patient covered by pair of inflatable thermal blankets that also schematically illustrates a forced-air heat pump for supplying heated air to the thermal blanket.

Turning now to FIG. 2, a pair of inflatable thermal blankets indicated by reference numeral 150 are shown as they might be placed over the patient's legs. Each thermal blanket 150 includes a primary inflatable covering 152 which is intended to be non-furlable (during use) and a suite of one or more secondary inflatable coverings which are furlable, there being three such coverings 154, 156 and 158 shown FIG. 2. The non-furlable covering is designed to remain non-furled throughout the course of a medical procedure. The furlable coverings are designed to be nominally furled but selectively unfurlable for inflation during a medical procedure, as discussed in more detail below. The structure and function of a similar inflatable thermal blanket may be understood with reference to U.S. Pat. No. 5,545,194, commonly assigned with this application.

The non-furlable covering 152 may be thought of as being subdivided into an inflatable section 160 surrounded by a non-inflatable section 162. The inflatable section 160 includes an inlet 180 that receives warmed air to pressurize and inflate it. The warmed air is provided by an airhose 182 from a forced-air heating unit 184 that includes a compressor 186 coupled to a heater 188. A control unit 190 controls the forced-air unit 184, and may include user-selectable fan speeds, controllable heat amounts, and temperature control. The inlet 180 in the inflatable section 160 may be provided with a cuff or other conventional connector adapted to receive and retain the distal end 183 of the airhose 182. Using this configuration, pressurized and heated air can flow through the airhose 182 into the inflatable section 160.

Figure 3:
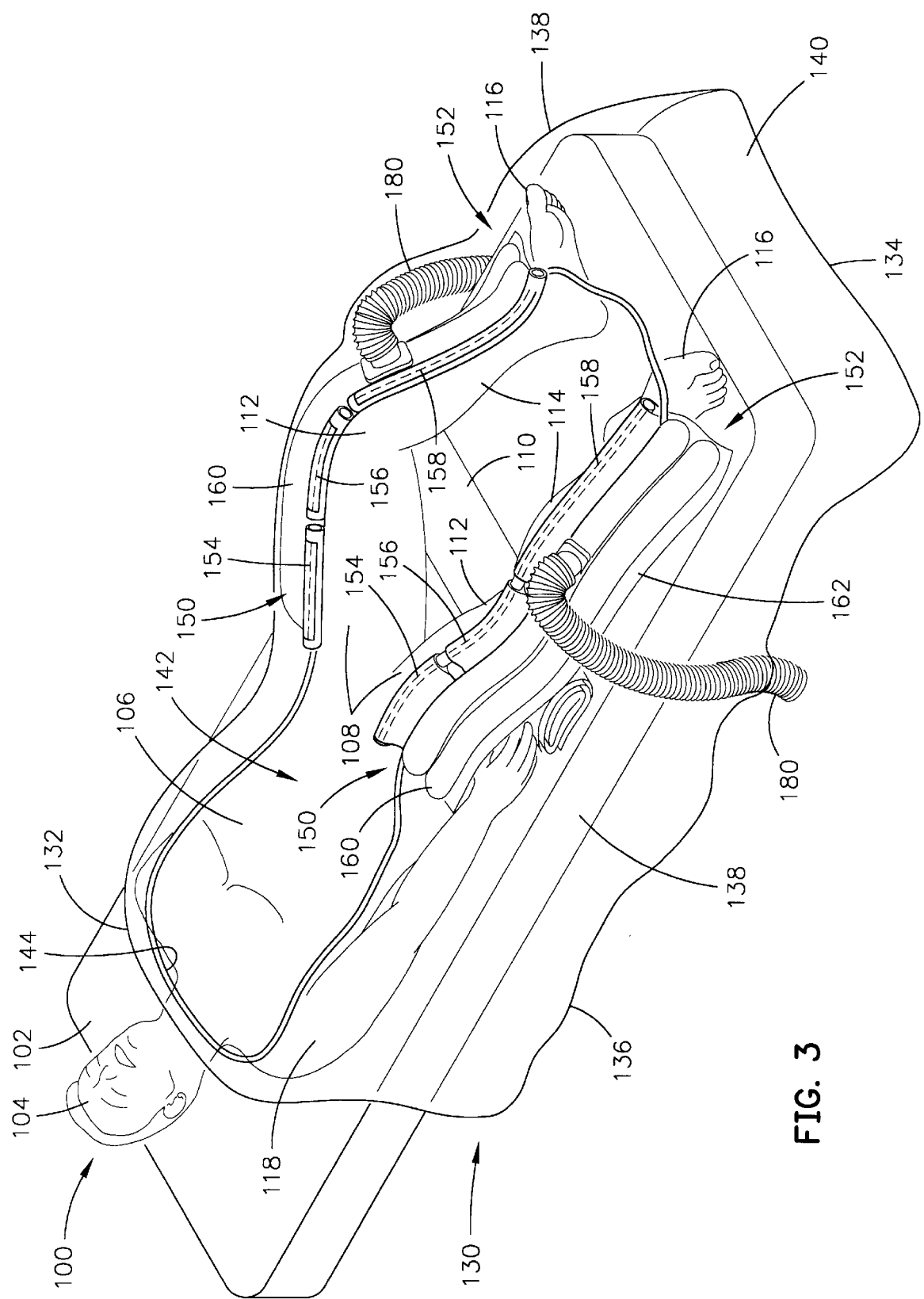
FIG. 3 is a perspective view of a supine patient covered by the surgical drape and the pair of inflatable thermal blankets shown in FIGS. 1 and 2, with the blankets in a furled state.

FIG. 3 illustrates the inflatable thermal blankets 150 in their furled configuration mounted on a cardiac patient and covered by the surgical drape 130. In this position, each airhose 180 is connected to a corresponding blanket and delivers temperature controlled air thereto. This inflates the non-furlable coverings 152 and, as described below, thermally bathes the outer and top portions of the patient's thighs 108 and lower legs 114 with the temperature controlled air. With the thermal blankets 150 in the furled position, the inner portions of the patients thighs 108 and lower legs 114 are not covered by the blankets and are accessible by a surgeon, for example, in order to remove vein sections from the patient's legs and transfer them to the patient's heart.

Figure 4:
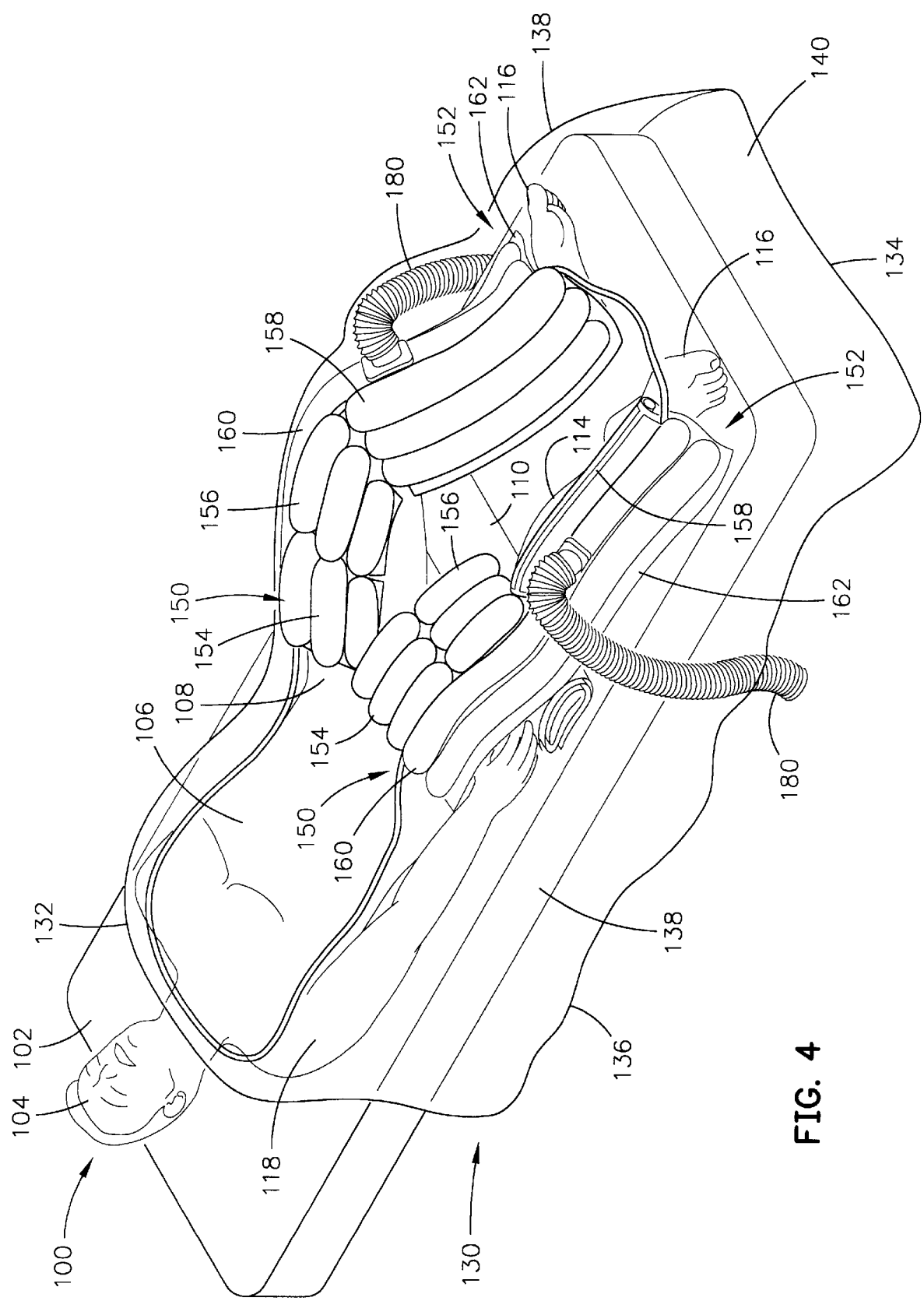
FIG. 4 is a perspective view of a supine patient covered by the surgical drape and the pair of inflatable thermal blankets shown in FIGS. 1 and 2, with the blankets in an unfurled state.

Turning now to FIG. 4, when the vein removal procedure is completed, the inner portions of the patient's thighs 108 and lower legs 114 can be covered for thermal treatment by unfurling the furlable coverings 154, 156 and 158 of the blankets 150. Not all of the furlable coverings need to be unfurled at the same time. For example, if access is only required to one of the patient's lower legs 114, only the furlable covering 158 which covers that leg would need to be furled during the procedure, as shown in FIG. 4. The remaining furlable coverings could all be unfurled at the outset, when the blankets are first set up.

When the furlable coverings 154, 156, 158 are unfurled, they become inflated extensions of the non-furlable coverings 152 of the blankets 150. More specifically, the furlable coverings unfurl and inflate to become extensions of the inflatable sections 160 and the peripheral non-inflatable sections 162 of the thermal blankets 150, as described in more detail below.

The inflatable thermal blankets of this invention may be constructed using methods and materials that are known for making similar products. A description of construction details suitable for making the thermal blankets of this invention is found in commonly-assigned U.S. Pat. No. 5,405,371, which has been incorporated by reference herein.

Figure 5:
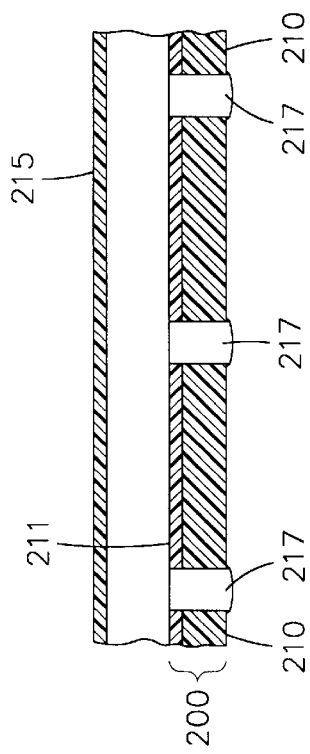
FIG. 5 is a partial cross-sectional view taken through an inflated section of the inflatable thermal blankets of FIG. 2.

With reference now to the incorporated U.S. Pat. No. 5,405,371 blanket and to FIG. 5 herein, the thermal blanket 150 is assembled from a base sheet 200 having a laminated structure in which a bottom layer 210 comprises a fibrous, preferably non-woven structure composed of synthetic or natural materials. A top layer 211, comprising a sheet of synthetic material, is disposed on and laminated to a surface of the bottom layer 210. For example, the bottom layer 210 may be a non-woven, hydroentangled polyester material and the top layer may include a polypropylene film that is extrusion-coated on to the polyester layer. Alternatively, the bottom layer 210 may comprise a non-woven, paper-based material to which a top layer including either a polyethylene or a polypropylene film has been glue laminated. Alternatively, the base sheet may be a single layer, of non-woven material for example. To form one or more inflatable chambers, an upper sheet 215 of material is attached at a plurality of locations to the top layer 211. Preferably, the upper sheet 215 comprises the same material as the top layer 211 of the base sheet 200. The upper sheet 215 is attached to the top layer 211 in the preferred embodiment in a continuously-running web process that includes stations at which the upper sheet 215 is heat-bonded to the top layer 211 to form the inflatable and non-inflatable sections of the thermal blanket 150.

Figure 6:
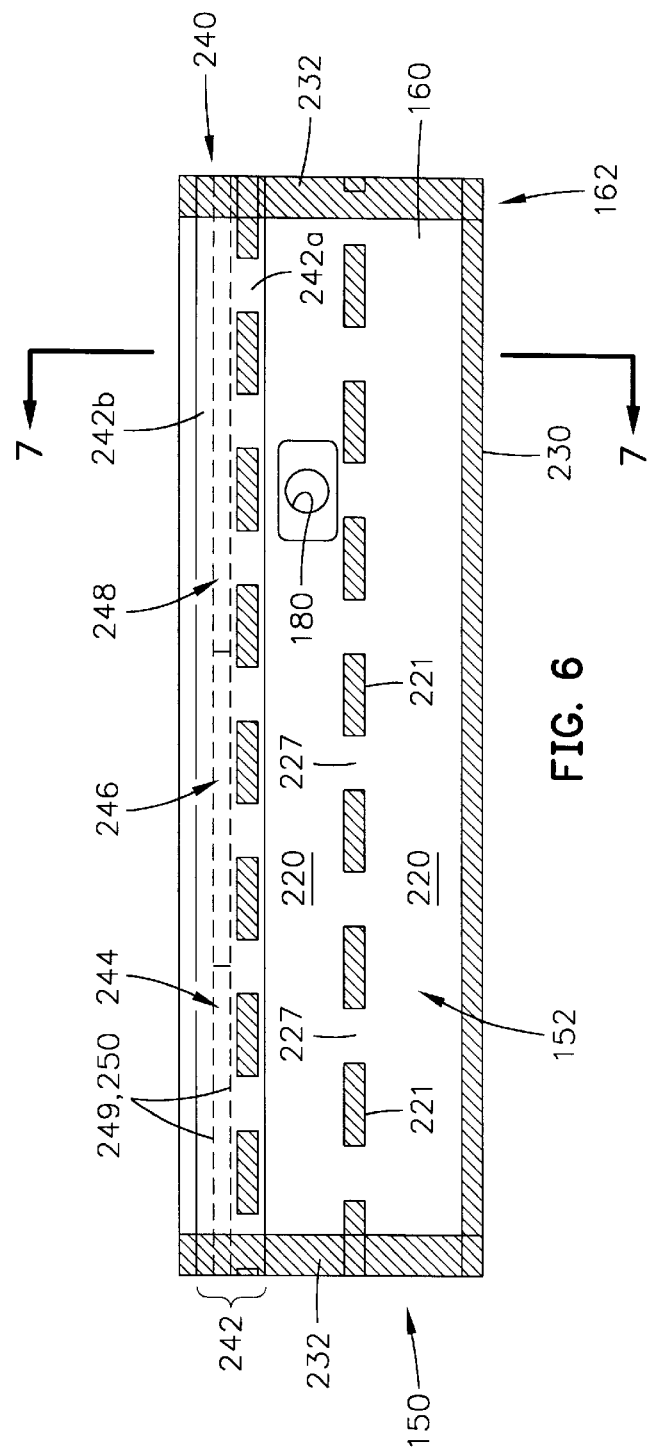
FIG. 6 is a plan view of an inflatable thermal blanket for the leg of a cardiac patient, with the blanket in a furled state.

Turning now to FIG. 6, the inflatable chambers are shown as having a generally elongate tubular shape. The inflatable chambers (which form the inflatable section 160) are indicated by reference numeral 220. The inflatable chambers 220 are preferably formed by discontinuous elongate heat seals. One example of an elongate discontinuous heat seal is shown having sealed portions 221 and unsealed portions 227. At the sealed portions 221 of the discontinuous elongate heat seal, the top layer 211 of the base sheet 200 is bonded to the upper sheet 215 in an elongate, air impermeable seam. Where the discontinuities 227 occur, air may circulate laterally between inflatable chambers. These discontinuities provide communication between the inflatable chambers, permitting pressurized, warmed air to circulate from the inlet 180 to, and through, the inflatable chambers 220. It should be understood that the inflatable chambers could be formed by a plurality of stake-point seals (as described in more detail below) or by longer elongate seals. The plurality of apertures 217 that open through the base sheet 200 exhaust pressurized warmed air from the inflatable chambers 220 underneath the thermal blanket to bathe the patient 100 in a warmed ambient atmosphere.

Figure 9:
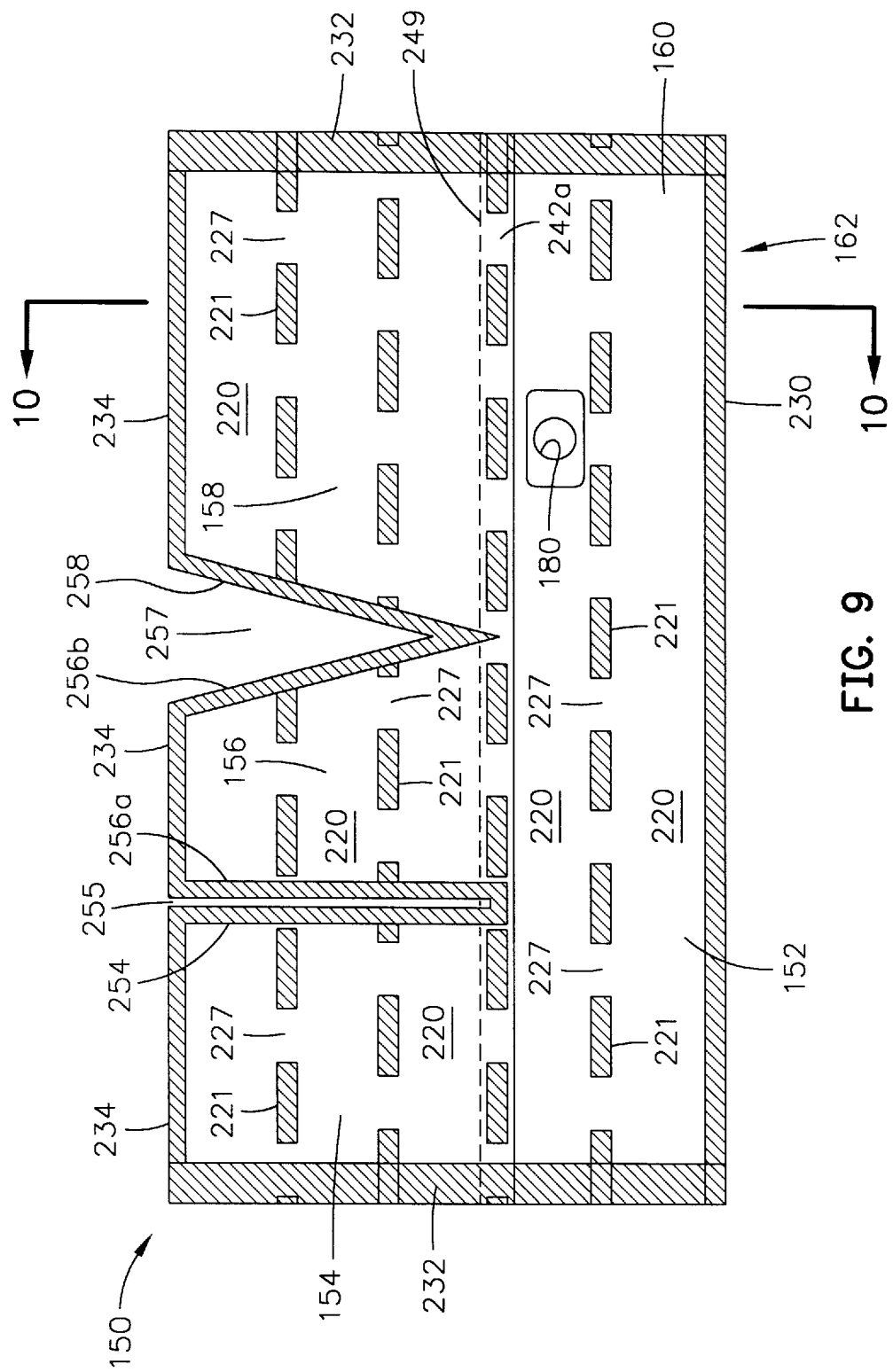
FIG. 9 is a plan view of an inflatable thermal blanket for the leg of a patient, with the blanket in an unfurled state.

Continuous, air impervious seals are shown in the top plan view of the thermal blanket 150 in FIGS. 6 and 9. These continuous air-impervious seals form the uninflatable section 162 of the thermal blanket 150. As shown in FIG. 6, there is a continuous, air-impervious edge seal 230 that is near one side of the non-furlable covering 152 and two continuous, air-impervious end seals 232 at either end of the covering 152. As shown in FIG. 9, the end seals are shown as continuing into the non-furlable coverings 154 and 158. A continuous, albeit serpentine, air impervious edge seal 234 is formed near the sides of the furlable coverings 154, 156 and 158 of the thermal blanket 150. The perimeter of the thermal blanket 150 is therefore sealed by a continuous, air-impervious seal comprising the seals 230, 232 and 234. These seals define the uninflatable section 162 of the thermal blanket 150. The inflatable chambers 220, in turn, define the inflatable section 160 of the thermal blanket and extend throughout the non-furlable and furlable coverings.

Figure 8:
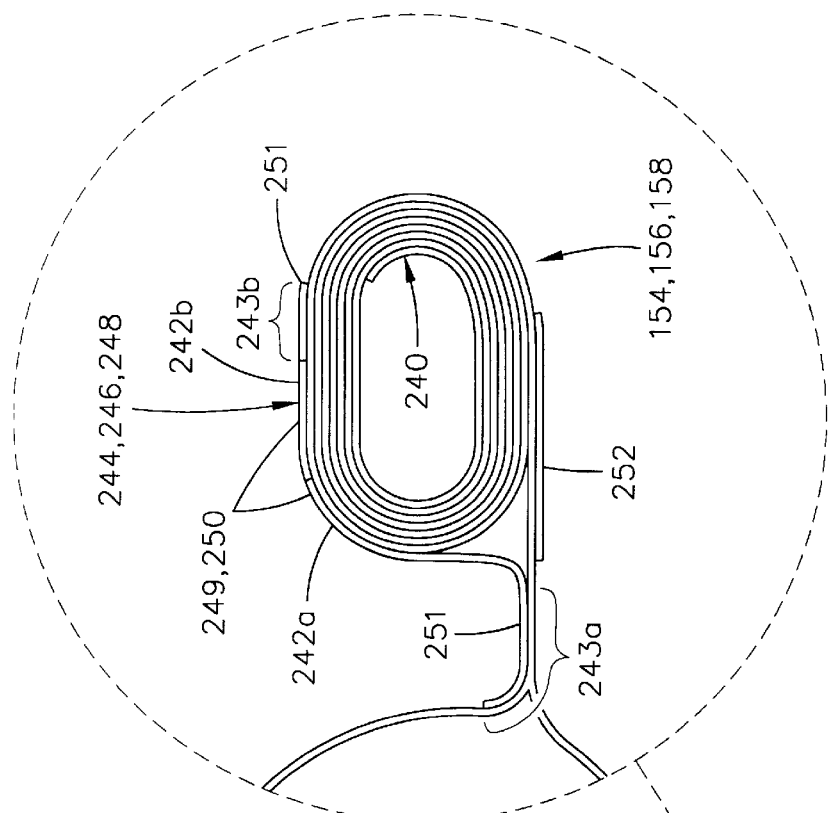
FIG. 8 is an enlargement of a portion of the cross-sectional view of FIG. 7.
Figure 7:
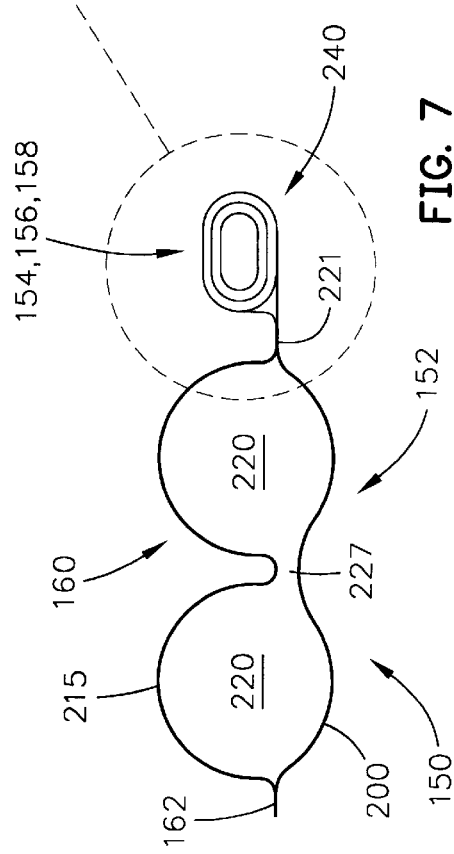
FIG. 7 is a cross-sectional view taken along line A—A in FIG. 6.

FIGS. 6–11 illustrate construction details which more specifically define the configuration and function of the non-furlable and furlable coverings of the thermal blanket 150. In FIGS. 6, 7 and 8, the thermal blanket 150 is shown in a furled state in which the non-furlable covering 152 is ready to be inflated by introducing air through the inlet 180. The invention contemplates that the furlable coverings 154, 156 and 158 will be controlled so that they will only inflate on command. Many forms of control devices, such as a system of valves, could be used. However, for reduced cost and ease of manufacture, a preferred control device places the furlable coverings in a furled state in which they are rolled and retained as indicated at 240 and as shown in detail in FIGS. 7 and 8. The furlable coverings are maintained in the rolled and retained stated by a retaining strip 242 which is preferably made from the same material as the base sheet 200, and which is adhered to the upper sheet by an adhesive strip or the like. The retaining strip 242 extends longitudinally between the seams 232 at the ends of the blanket 150, as shown in FIG. 6.

As shown in FIG. 8, the retaining strip 242 includes a first portion 242a that is adhered to the upper sheet 215 at 243a. It covers one row of the elongate discontinuous heat seals but does not interfere with the passage of air between the discontinuities 227 therein. This allows air to freely pass through the discontinuities when the blanket 150 is unfurled. However, as can be seen in FIG. 8, when the furlable coverings 154, 156 and 158 are rolled and retained, air is prevented from entering into the furlable coverings and they will not inflate. The retaining strip 242 includes a second portion 242b that is adhered to the base sheet 200 at 243b. In order to provide for selective unfurling of the furlable coverings 154, 156 and 158, a release device is used. While many forms of release device could be implemented, it is preferable to use zip strip sections 244, 246 and 248, which correspond to the furlable coverings 154, 156 and 158, and which are centrally formed in the retaining strip 242. These zip strip sections are tear-away strips which, when torn away, longitudinally separate the retaining strip portions 242a and 242b so as to release the corresponding furlable coverings 154, 156 and 158 from their rolled and retained positions. The zip strip sections are preferably formed by two parallel rows of perforations 249 and 250 extending longitudinally between the seams 232 at the ends of the blanket 150.

If desired, an adhesive strip 152 can be provided to help secure the blanket 150 during surgery. The adhesive strip 152 can be formed by applying adhesive on the bottom surface of the base sheet 200, at a location which is approximately below the retaining strip 242. This adhesive is then covered by a peelable backing strip such that the adhesive is prevented from adhering until it is ready for use. The lower adhesive strip 152 is useful for securing the blanket 150 to the patient.

FIGS. 9, 10 and 11 illustrate the blanket 150 with the furlable coverings 154, 156 and 158 in an unfurled position and ready to be inflated by receiving air from the non-furlable covering 152, which in turn receives air through the inlet 180. The zip strip sections have now been torn away at the perforations 249 and 250 so as to leave only the retaining strip portions 242a and 242b attached to the upper and base sheets of the blanket 150, respectively, as shown in FIGS. 10 and 11. With the retaining strip portions 242a and 242b detached from one other, the furlable coverings 154, 156 and 158 portions will unfurl and inflate under the force of the inflating medium being delivered through the unsealed portions 227 of the discontinuous elongate seals that underlie the retaining strip 242. In this regard, it will be recalled that the retaining strip 242 is only secured to the upper sheet 215 and base sheet 200 of the blanket 150 at locations 243a and 243b, as shown in FIG. 8. The furlable coverings will remain rolled and retained only when the retaining strip is intact between these two attachment locations. Once the retaining strip 242 is separated, there is nothing to prevent the force of the inflating medium from distending the furlable coverings from their rolled and retained positions. It will be seen that the furlable coverings, when unfurled, form extensions of the inflatable section 160 of the blanket 150, and include a continuation of the pattern of inflatable chambers 220 and discontinuous elongate heat seals, having sealed portions 221 and unsealed portions 227, that were noted above in connection with the non-furlable covering 152.

The furlable coverings also form an extension of the non-inflatable section 162 of the blanket 150. As shown in FIG. 9, the furlable covering 154 is shown as being peripherally defined by one of the end seals 232 and the edge seal 234, which includes a continuous, air-impervious transverse seal portion 254. A transverse gap 255 separates the furlable covering 154 from the adjacent furlable covering 156. The furlable covering 156 is peripherally defined by the edge seal 234, which includes a pair of continuous, air-impervious transverse seal portions 256a and 256b. The transverse seal portion 256a is parallel to the transverse seal portion 254 and is separated therefrom by the transverse gap 255. The transverse seal portion 256b is angled relative to the transverse seal portion 256a. It defines one side of a V-shaped (i.e., wedge-shaped) gap 257 that separates the furlable coverings 156 and 158. The other side of the wedge-shaped gap 257 is defined by an angled transverse seal portion 258 of the edge seal 234, which is also continuous and air-impermeable, and which intersects the transverse seal portion 256b at a location which is below the retaining strip portion 242a. The edge seal 234, including the transverse seal portion 258, together with the end seal 232, define the periphery of the furlable covering 158.

As can be seen in FIG. 4, the furlable covering 154 is ideally suited for covering the upper portion of the patient's thighs 108, as well as the patient's groin area. The furlable covering 156 is ideally suited for covering the lower portion of the patient's thighs 108, while the furlable covering 158 is ideally suited for covering the patient's lower legs 114. Advantageously, the wedge-shaped gap 257 allows the furlable coverings 154 and 156 to follow the contour of the patient's legs when the legs are bent.

Figure 12:
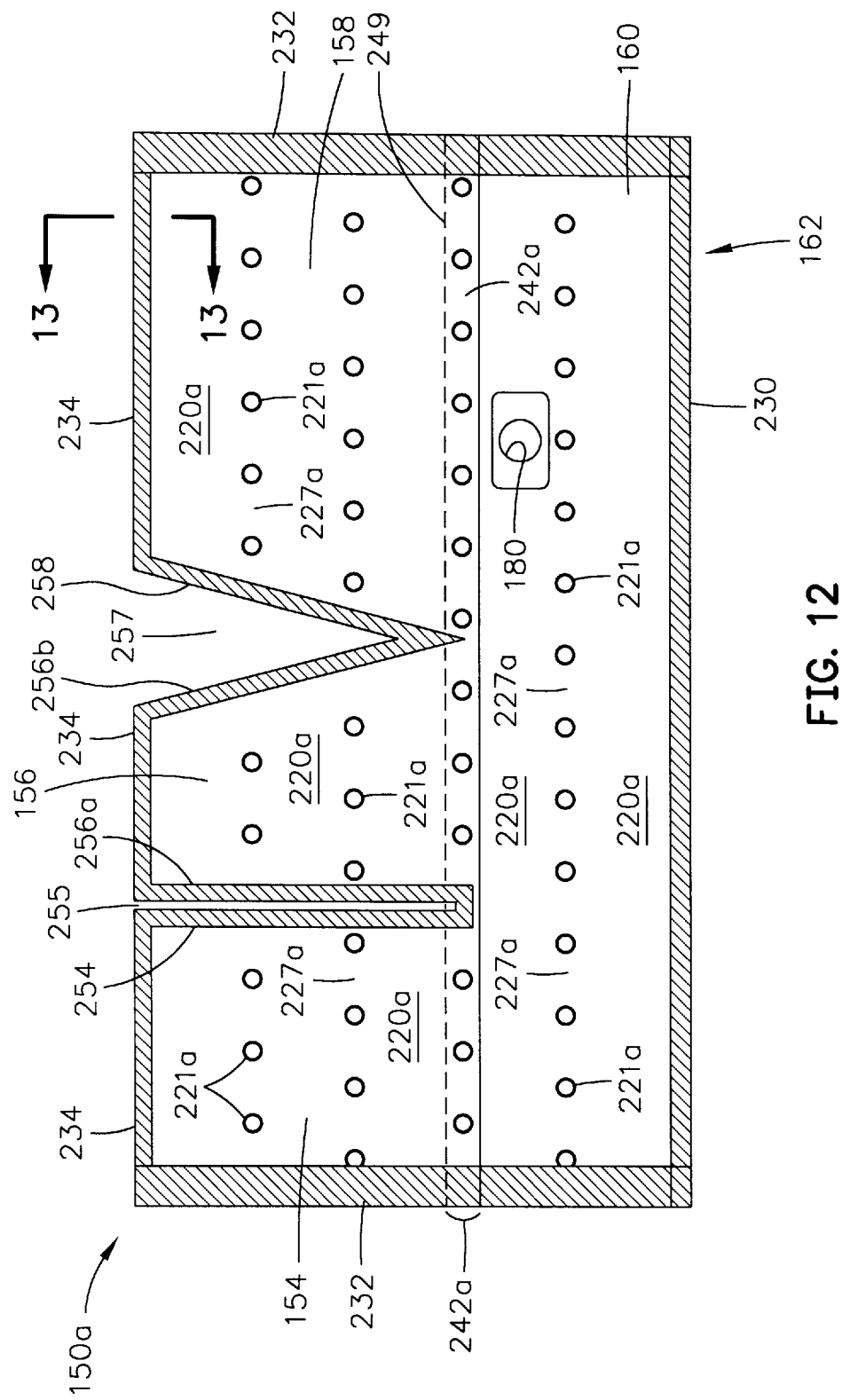
FIG. 12 is a plan view of an inflatable thermal blanket according to another aspect of the invention for the leg of a patient, with the blanket in an unfurled state.
Figure 13:
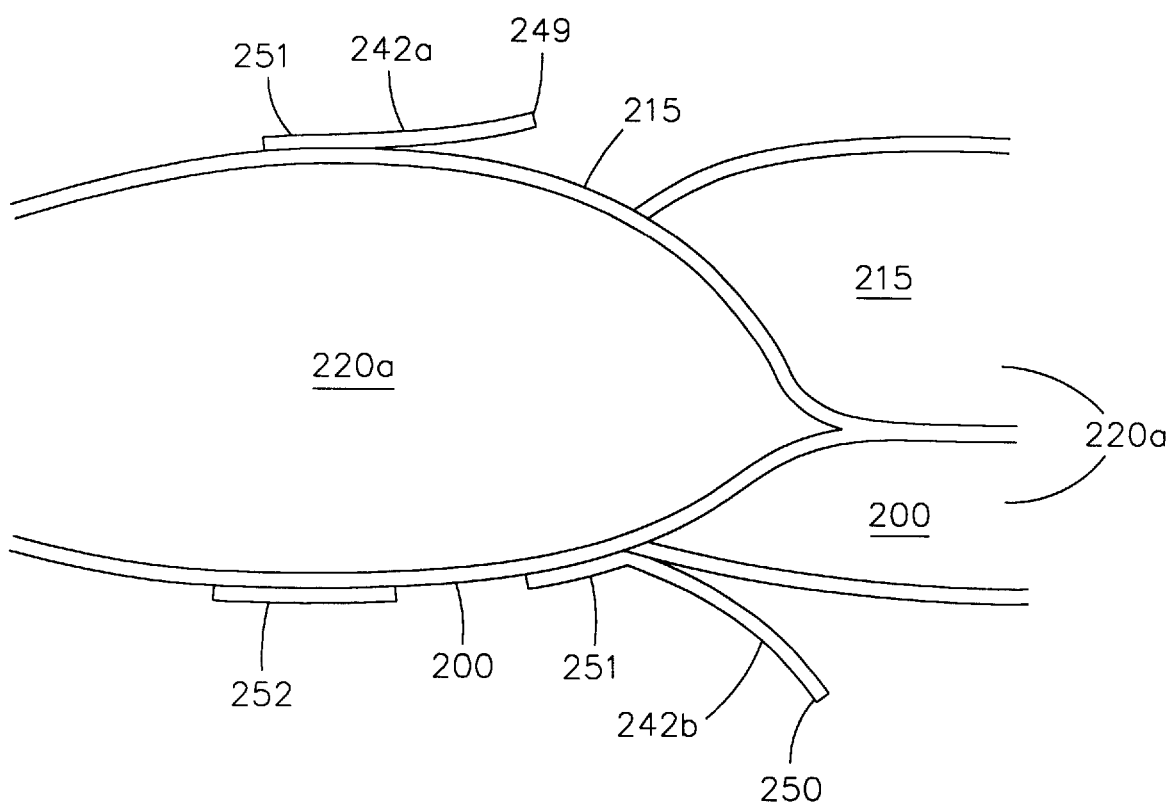
FIG. 13 is a cross-sectional view taken along line C—C in FIG. 11.

FIGS. 12 and 13 illustrate a thermal blanket 150a representing an alternative construction of the thermal blanket 150. The thermal blanket 150a is similar in most respects to the thermal blanket 150 and corresponding elements are shown using like reference numbers. The principal difference in the thermal blanket 150a is that the instead of using elongate seal portions 221 and unsealed portions 227 to form the discontinuous elongate heat seals, point seals 221a and unsealed portions 227a are used. Preferably, the point seals 221a are longitudinally aligned in parallel rows so as to form inflatable chambers 220a. The point seals 221a are transversely aligned in parallel rows that are not necessarily perpendicular to the longitudinal rows. This construction results in the inflatable chambers 220a being somewhat discrete rather than tubular in shape, as is the case with the inflatable chambers 220 of the blanket 150. As shown in FIG. 13, the result is a blanket that has a quilted appearance.

Figure 14:
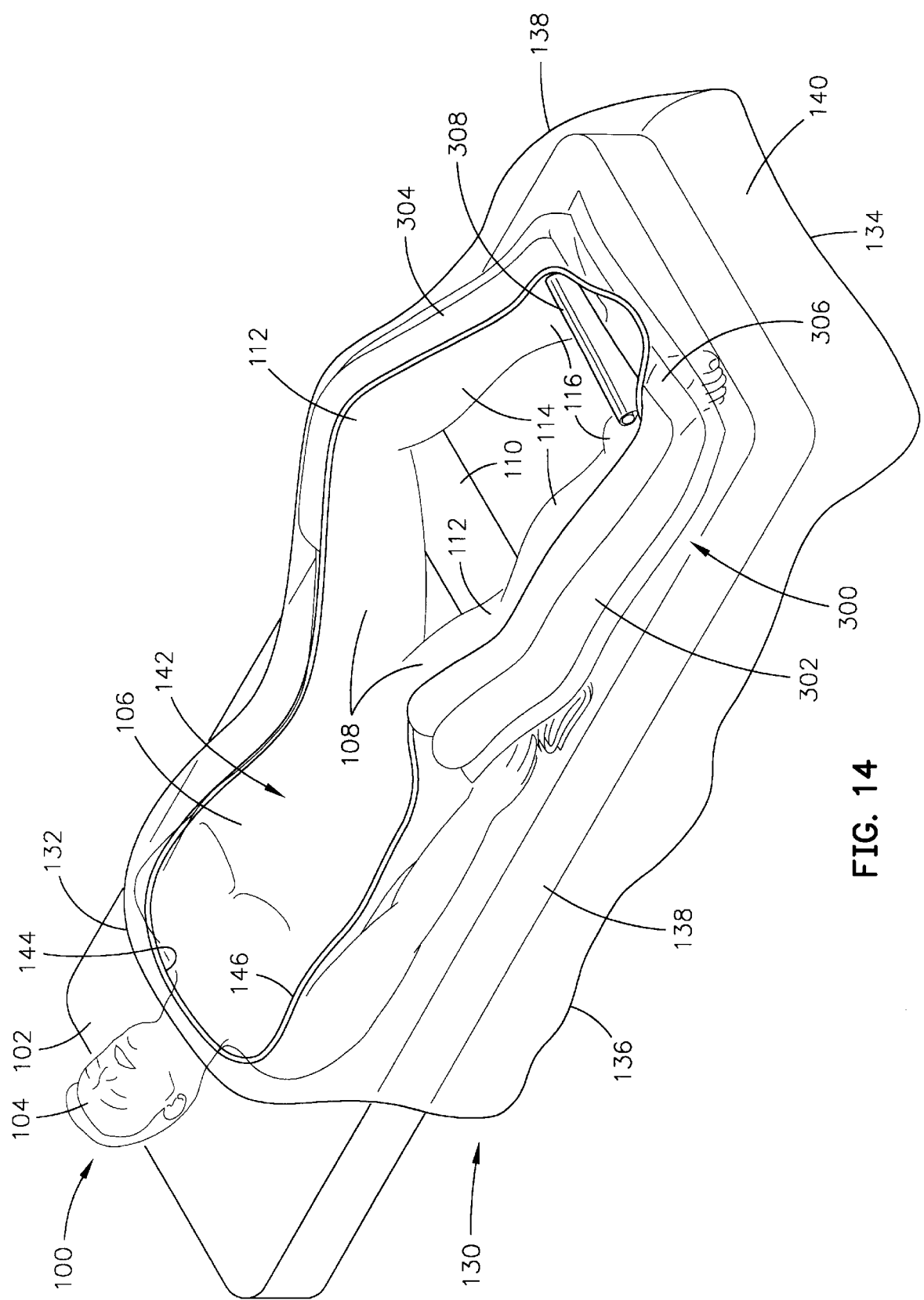
FIG. 14 is a perspective view of a supine patient covered by a surgical drape and an inflatable thermal blanket according to another aspect of the invention, with the blanket in a furled state.
Figure 15:
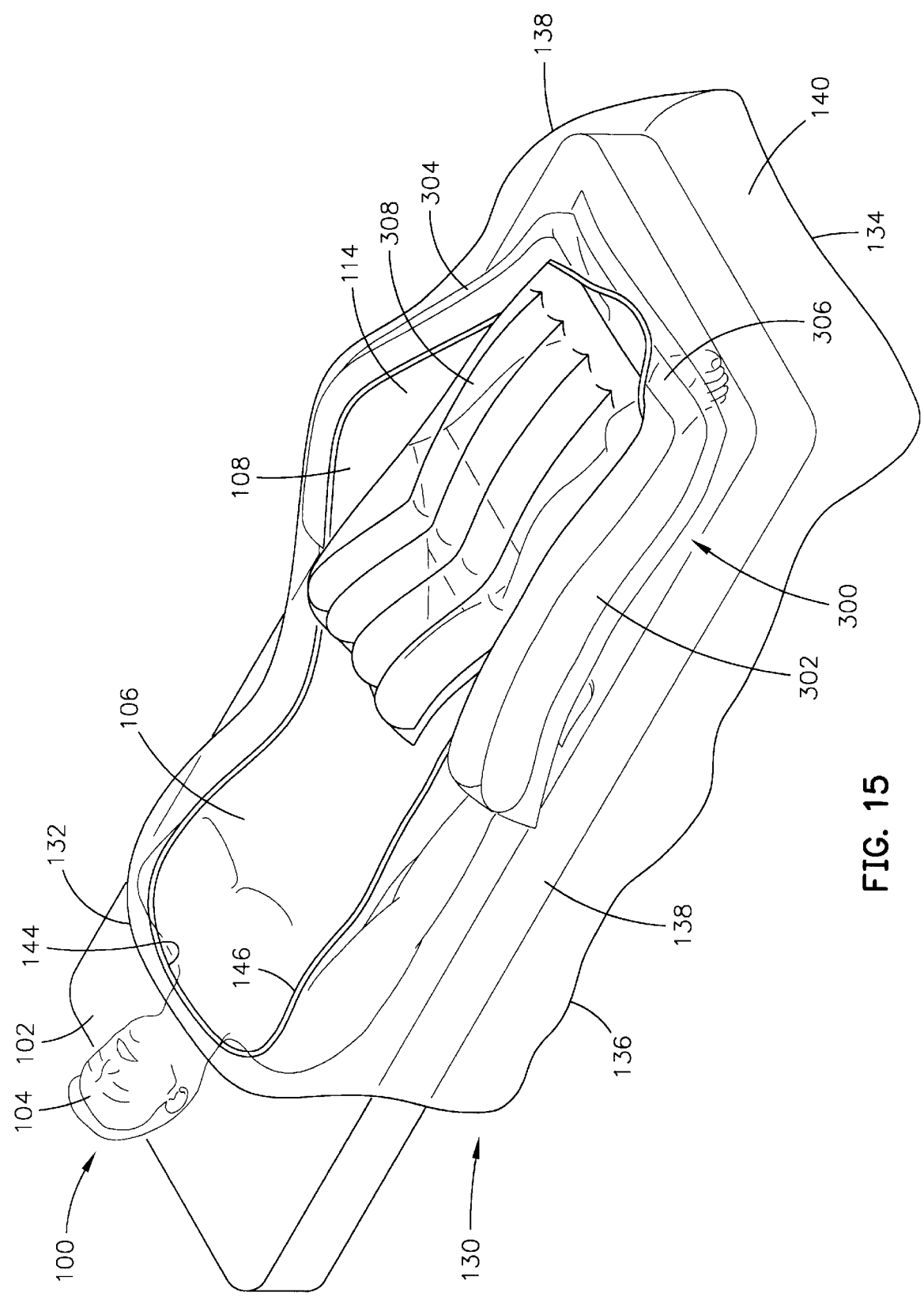
FIG. 15 is a perspective view of a supine patient covered by a surgical drape and an inflatable thermal blanket as shown in FIG. 14, with the blanket in an unfurled state.

Turning now to FIGS. 14 and 15, another embodiment of the invention is shown in which a single blanket 300 is used on the patient 100 in place of two blankets 150 or 150a. The construction details of the blanket 300 are the same as those used in fabricating the blankets 150 or 150a. The shape of the blanket 300, however, is somewhat different. The blanket 300 includes interconnected, preferably integral, non-furlable coverings 302, 304 and 306, and a furlable covering 308. The non-furlable covering 302 defines a first non-furlable lateral portion of the blanket 300 that extends generally parallel to and lateral to one of the patient's legs. The non-furlable covering 304 defines a second non-furlable lateral portion of the blanket 300 that extends generally parallel to and lateral to another one of the patient's legs. The non-furlable covering 306 defines a non-furlable base portion of the blanket 300 that connects the two non-furlable lateral portions and extends generally perpendicular thereto over the patient's feet.

The furlable covering 308 is formed as an extension of the non-furlable covering 306. It is nominally furled in a rolled and retained position as shown in FIG. 14, whereas the non-furlable coverings are nominally unfurled and ready to be inflated in the manner shown in FIG. 14 when positioned for use during a cardiac procedure. The furlable covering 308 is preferably rolled and retained using a retaining strip in identical fashion to the furlable coverings of the blankets 150 and 150a. As shown in FIG. 15, when the retaining strip is removed, the furlable covering 308 unrolls under the force of the inflating medium and inflates to cover portions of the patients legs and groin area.

Figure 16:
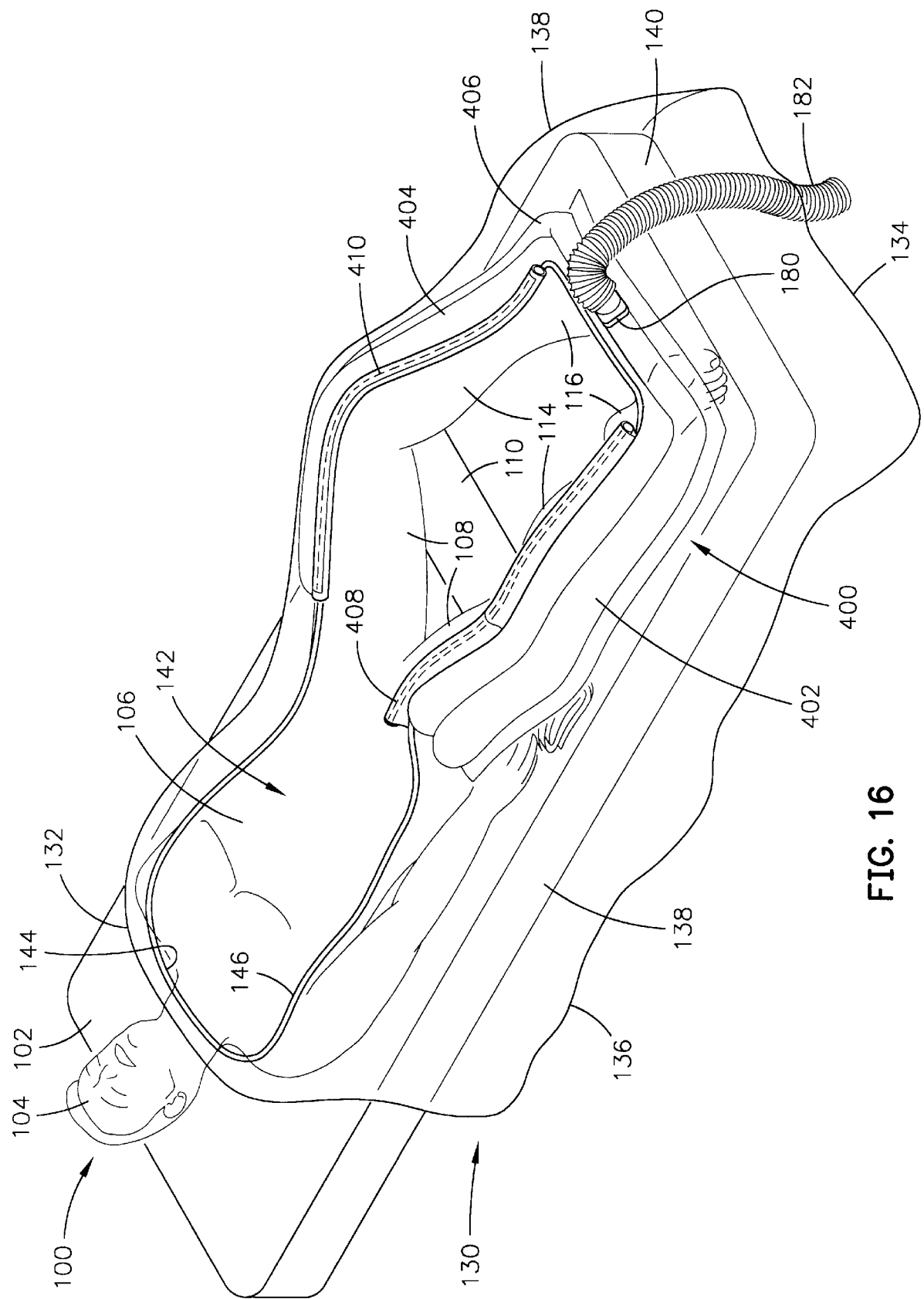
FIG. 16 is a perspective view of a supine patient covered by a surgical drape and an inflatable thermal blanket according to another aspect of the invention, with the blanket in a furled state.
Figure 17:
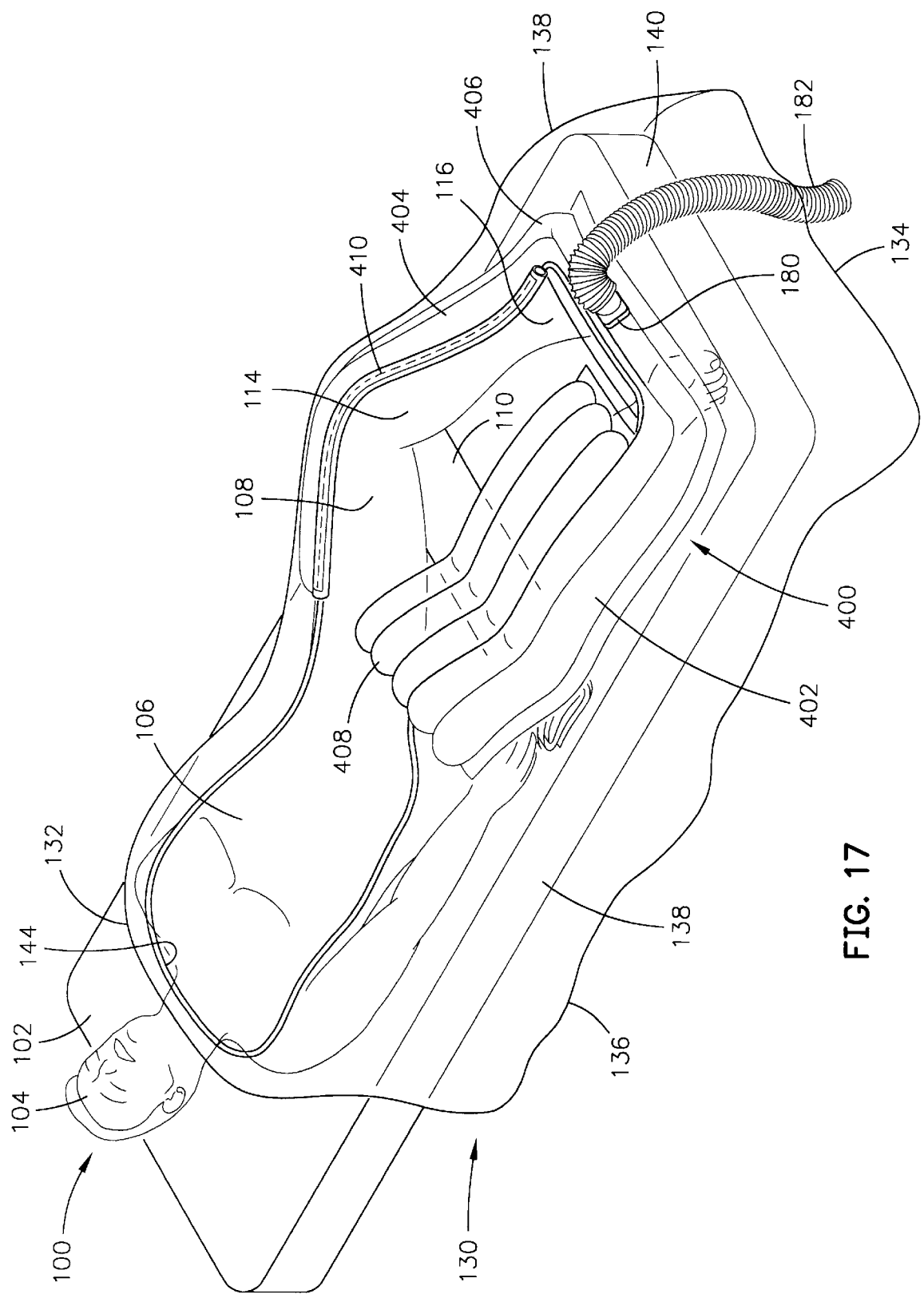
FIG. 17 is a perspective view of a supine patient covered by a surgical drape and an inflatable thermal blanket as shown in FIG. 16, with the blanket in an unfurled state.

Turning now to FIGS. 16 and 17, another embodiment of the invention is shown in which a single blanket 400 is used on the patient 100 in place of two blankets 150 or 150a. The construction details of the blanket 400 are the same as those used in fabricating the blankets 150 or 150a. The shape of the blanket 400, however, is somewhat different from that of the blankets 150 and 150a and somewhat similar to that of the blanket 300. The blanket 400 includes non-furlable coverings 402, 404 and 406, and two suites of furlable coverings 408 and 410, each comprising one or more separately unfurlable coverings. The non-furlable covering 402 defines a first non-furlable lateral portion of the blanket 400 that extends generally parallel to and lateral to one of the patient's legs. The non-furlable covering 404 defines a second non-furlable lateral portion of the blanket 400 that extends generally parallel to and lateral to another one of the patient's legs. The non-furlable covering 406 defines a non-furlable base portion of the blanket 400 that connects the two lateral non-furlable portions and extends generally perpendicular thereto over the patient's feet. It supports the air inlet 180 to which is connected the inlet hose 182.

The first furlable covering suite 408 is formed as an extension of the first lateral non-furlable covering 402. The second furlable covering suite 410 is formed as an extension of the second lateral non-furlable covering 404. Both furlable covering suites are nominally furled in a rolled and retained position as shown in FIG. 16, whereas the non-furlable coverings are nominally unfurled and ready to be inflated in the manner shown in FIG. 16 when positioned for use during a cardiac procedure. The furlable covering suites 408 and 410 are preferably rolled and retained using retaining strips in identical fashion to the furlable coverings of the blankets 150 and 150a. As shown in FIG. 17, when the retaining strips are removed, the furlable covering suites unroll under the force of the inflating medium and inflate to cover portions of the patients legs and groin area. One advantage of the thermal blanket 400, as well as the thermal blanket 300, is that only a single air inlet and heater hose are required by virtue of the common base portion that distributes air to both lateral portions of those blankets.

The description and illustrations make clear that the system of this invention may or may not include a surgical drape made from one or more sheets of material. It should be evident that such a drape will aid in trapping and retaining warmed air about a patient's legs, while performing the usual barrier functions of a surgical drape. Moreover, the drape's shape, size, configuration, and structure may be selectively varied to fit particular circumstances, patients, and clinical requirements, without departing from the scope of spirit of this invention.

Other embodiments and modifications of this invention may occur to those of ordinary skill in the art in view of these teachings. Therefore, this invention is to be limited only by the following claims, which include all such embodiments and modifications when viewed in conjunction with the above specification and accompanying drawings.

We claim:

1. A system for warming a patient during surgery, comprising:
    a source of heated air;
    one or more inflatable thermal blankets, each comprising:
        an upper sheet and an air-permeable base sheet connected together at a plurality of locations to form a first inflatable covering;
        an air inlet in the first inflatable covering for receiving a temperature-controlled inflating medium from the source of heated air;
        the first inflatable covering being adapted to inflate upon the inflating medium being introduced into the air inlet;
        the first inflatable covering configured for disposition proximate a portion of at least one of the patient's legs;
        a second inflatable covering attached to the first inflatable covering, the second inflatable covering being adapted to remain initially uninflated upon the inflating medium being introduced into the air inlet; and
        a control device for controllably allowing the inflating medium to flow from the first inflatable covering to the second inflatable covering to inflate the second inflatable covering; and
    a surgical drape adapted to be disposed over the patient and the first inflatable covering.

2. The system of claim 1, wherein the surgical drape has a central aperture therein defining an opening for providing medical access to the patient.

3. The system of claim 2, wherein the second inflatable covering is positioned to extend into the opening when the second inflatable covering is inflated.

4. The system of claim 1, wherein the central aperture is generally rectangular and sized such that the opening extends from the patient's upper chest area to the patient's lower legs.

5. The system of claim 1, further including one or more attachment devices for securing the surgical drape to the one or more thermal blankets.

6. The system of claim 1, further including one or more attachment devices for securing the one or more thermal blankets to the patient.

7. The system of claim 1, including two of the inflatable thermal blankets, each of the inflatable thermal blankets being configured to warm a respective one of the patient's legs and being arranged such that the first inflatable coverings are positioned over the lateral portions of the patient's legs and the second inflatable coverings are positioned so as to extend over the top and inner portions of the patients legs when the second inflatable portions are inflated.

8. The system of claim 7, wherein each of the two inflatable thermal blankets includes plural second inflatable coverings.

9. The system of claim 8, wherein each of the two inflatable thermal blankets includes a control device for separately inflating each of the second inflatable coverings.

10. The system of claim 9, wherein each of the two inflatable thermal blankets is configured for mounting over a respective leg of the patient, wherein there are three second inflatable coverings respectively configured so as to extend over the patient's groin and upper thighs, the patient's mid and lower thighs, and the patient's lower legs, when the second inflatable coverings are inflated.

11. A system for warming a patient comprising:
    a source of heated air;
    an inflatable thermal blanket comprising:
        a first inflatable covering formed from an upper sheet and an air-permeable base sheet connected together at a plurality of locations;
        the first inflatable covering having a central base portion and two lateral portions extending generally perpendicularly from the base portion and generally parallel to each other;
        an inlet in the base portion of the first inflatable covering for receiving a temperature-controlled inflating medium from the source of heated air;
        the first inflatable covering being adapted to inflate upon the inflating medium being introduced into the air inlet;
        a second inflatable covering attached to the first inflatable covering, the second inflatable covering being adapted to remain initially uninflated upon the inflating medium being introduced into the air inlet; and
        a control device for controllably allowing the inflating medium to flow from the first inflatable covering to the second inflatable covering to inflate the second inflatable covering; and
    a surgical drape adapted to be mounted over the first covering.

12. The system of claim 11, wherein the second inflatable covering is attached to the base portion of the first inflatable covering.

13. The system of claim 11, wherein there are two suites of the second inflatable coverings which are respectively attached to the lateral portions of the first inflatable covering.

14. The system of claim 13, wherein the suites each comprise plural ones of the second inflatable coverings.

15. A method for warning a patient with an inflatable thermal blanket, the inflatable thermal blanket including:
    a first inflatable covering including an upper sheet and an air-permeable base sheet connected together at a plurality of locations;
    an inlet in the first inflatable covering for receiving a temperature-controlled inflating medium;
    the first inflatable covering being adapted to inflate upon the inflating medium being introduced into the air inlet;
    at least one second inflatable covering attached to the first inflatable covering, the second inflatable covering being adapted to remain initially uninflated upon the inflating medium being introduced into the air inlet; and a control device for controllably allowing the inflating medium to flow from the first inflatable covering to the second inflatable covering to inflate the second inflatable covering the method including the steps of:

placing the inflatable thermal blanket on a patient such that the first inflatable covering covers lateral portions of the patient's legs and the second inflatable covering is adjacent the top and inner portions of the patient's legs;

inflating the first inflatable covering by introduction of the inflating medium through the inlet; and operating the control device to inflate the second inflatable covering such that the second inflatable covering inflates to cover the inner portions of the patient's legs.

16. A method for treating a patient with a warming system, the warming system including:

a source of heated air;

one or more inflatable thermal blankets, each comprising:
 a first inflatable covering formed from an upper sheet and an air-permeable base sheet connected together at a plurality of locations;
 an inlet in the first inflatable covering for receiving a temperature-controlled inflating medium from the source of heated air;
 the first inflatable covering being adapted to inflate upon the inflating medium being introduced into the air inlet;
 the first inflatable covering configured for mounting over the outer and top portions of at least one of the patient's legs;
 a second inflatable covering attached to the first inflatable covering, the second inflatable covering being adapted to remain initially uninflated upon the inflating medium being introduced into the air inlet; and
 a control device for controllably allowing the inflating medium to flow from the first inflatable covering to the second inflatable covering to inflate the second inflatable covering; and a surgical drape adapted to be mounted over the patient and the first inflatable covering;

the method including the steps of:
 placing the one or more inflatable thermal blankets on a patient such that the inflatable covering covers the outer portions of the of at least one leg and the second inflatable covering is adjacent a top and inner portion of the at least one leg;
 placing the surgical drape over the first inflatable covering;
 inflating the first inflatable covering by introduction of the inflating medium through the inlet;
 operating the control device to inflate the second inflatable covering such that the second inflatable covering inflates to cover the top and inner portion of the at least one leg.

* * * * *